(12) United States Patent
Ismail et al.

(10) Patent No.: US 6,799,458 B2
(45) Date of Patent: Oct. 5, 2004

(54) OIL LEVEL/CONDITION SENSOR

(75) Inventors: Keith N. Ismail; Oscar Alfonso Lecea; Steven Douglas Thomson, all of El Paso, TX (US)

(73) Assignee: Delphi Technologies, Inc., Troy, MI (US)

(*) Notice: Subject to any disclaimer, the term of this patent is extended or adjusted under 35 U.S.C. 154(b) by 154 days.

(21) Appl. No.: 09/849,201

(22) Filed: May 4, 2001

(65) Prior Publication Data

US 2002/0162390 A1 Nov. 7, 2002

(51) Int. Cl.⁷ ............................................. G01F 23/00
(52) U.S. Cl. ................................. 73/304 C; 361/284
(58) Field of Search ..................... 73/304 R, 290 R, 73/304 C; 338/38; 340/620; 361/284; 324/663, 671

(56) References Cited

U.S. PATENT DOCUMENTS

| | | | | |
|---|---|---|---|---|
| 2,456,617 A | * | 12/1948 | Burch | 73/295 |
| 3,123,751 A | | 3/1964 | Balsbaugh | 361/280 |
| 3,524,116 A | | 8/1970 | Bray | 361/284 |
| 3,703,829 A | * | 11/1972 | Dougherty | 73/290 R |
| 3,735,638 A | * | 5/1973 | Miller | 73/304 R |
| 3,827,300 A | * | 8/1974 | Thaler | 73/304 C |
| 3,874,237 A | * | 4/1975 | Zwarts | 73/290 R |
| 4,203,408 A | | 5/1980 | Yamaguchi et al. | 123/198 |
| 4,392,378 A | | 7/1983 | Pitches et al. | 73/304 C |
| 4,507,521 A | * | 3/1985 | Goellner | 174/151 |
| 4,574,328 A | * | 3/1986 | Maier | 361/284 |
| 4,730,489 A | * | 3/1988 | Hoekstra | 73/304 C |
| 5,477,727 A | * | 12/1995 | Koga | 73/304 C |
| 6,178,817 B1 | * | 1/2001 | Hewelt et al. | 73/290 V |

FOREIGN PATENT DOCUMENTS

| | | | | |
|---|---|---|---|---|
| DE | 19511556 | | 7/1996 | |
| DE | 19757924 | | 7/1999 | |
| EP | 0102678 A | * | 4/1983 | 73/304 R |
| GB | 2136965 A | * | 9/1984 | 73/304 R |
| SU | 798576 | | 1/1981 | |

* cited by examiner

Primary Examiner—Hezron Williams
Assistant Examiner—Katina Wilson
(74) Attorney, Agent, or Firm—Jimmy L. Funke

(57) ABSTRACT

An oil level/condition sensor includes a first level sensing tube, a common tube, and a second level sensing tube. The tubes are concentric to each other around a central axis. Moreover, the tubes are separated by plastic spacers which insulate the level sensing tubes from the common tube and maintain the concentricity of the tubes. Installed in the end of the first level sensing tube is a coupling/plug and disposed around the coupling/plug is a first condition sensing tube. The coupling/plug insulates the first level sensing tube from the first condition sensing tube and prevents fluid communication therebetween. A second condition sensing tube is attached to the second level sensing tube around the common tube and the first condition sensing tube. A ring-shaped insulator electrically isolates the second condition sensing tube from the second level sensing tube. The multiple tube configuration provides increased sensing surface area without increasing the length of the sensor or dramatically increasing the overall diameter of the sensor package. As such, the increased sensing surface area increases the signal strength and the accuracy of the sensor. Thus, the sensor is used in relatively shallow oil pans where the length of the sensor is constrained by the depth of the oil pan.

10 Claims, 1 Drawing Sheet

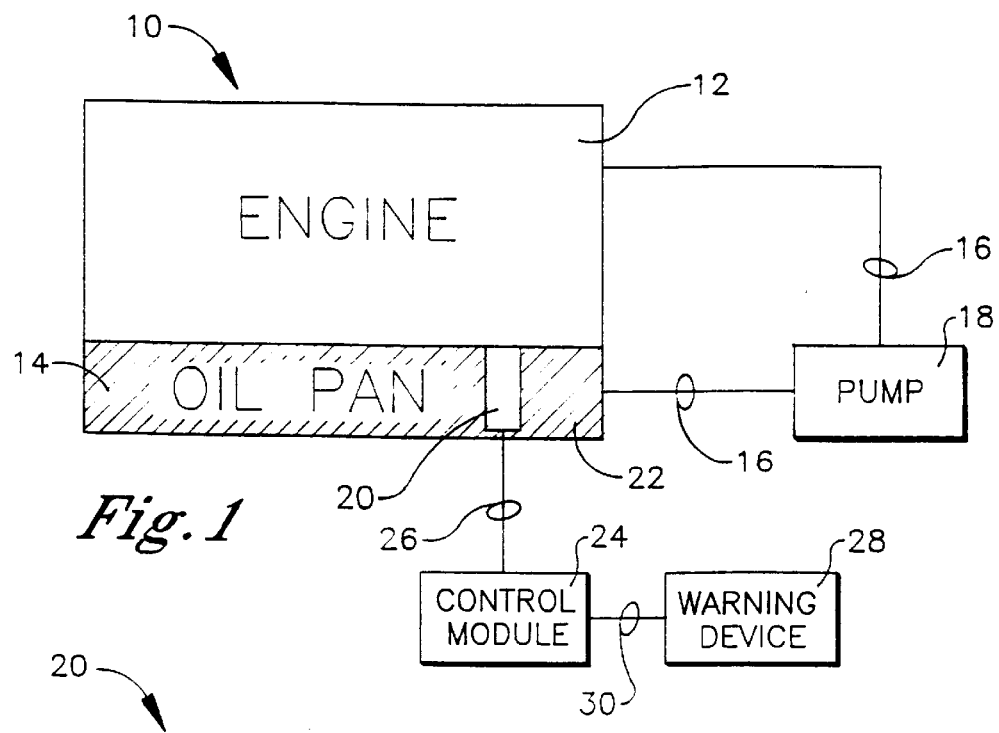
*Fig. 1*
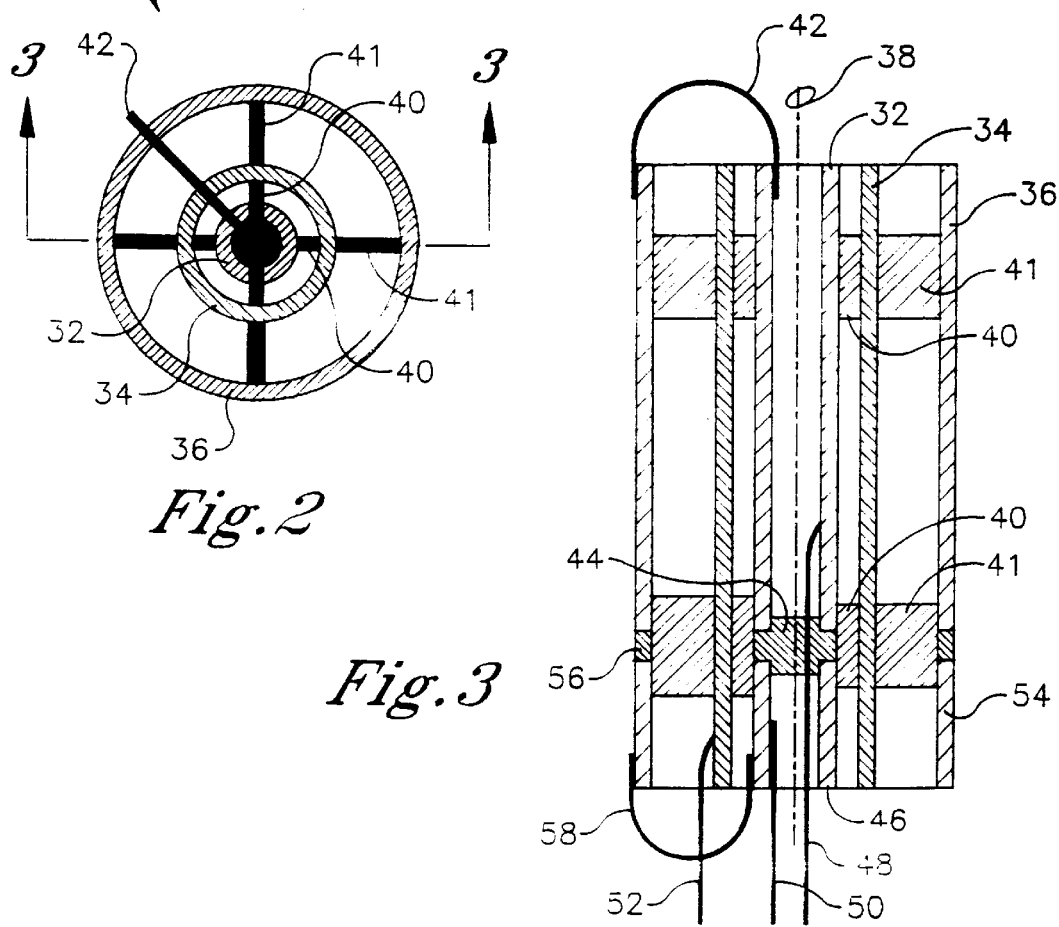
*Fig. 2*
*Fig. 3*

OIL LEVEL/CONDITION SENSOR

TECHNICAL FIELD

The present invention relates generally to engine oil sensors.

BACKGROUND OF THE INVENTION

Automatically monitoring the quality of oil in an engine alerts the owners or operators in a timely fashion when maintenance should be performed as dictated by the actual condition of the oil. Performing maintenance when it is actually required is preferred over following a predetermined, one-size-fits-all schedule that might be too long or too short for any given vehicle, depending on the way the vehicle is driven. If too long a period elapses between maintenance, a vehicle can be damaged. On the other hand, conducting maintenance when it is not needed is wasteful both in terms of labor and in terms of natural resources. For example, if a vehicle doesn't require an oil change but nevertheless receives one, oil is in effect wasted.

Accordingly, oil condition sensors, having a generally cylindrical shape, have been provided for measuring various parameters of lubricating oil, and to generate warning signals when maintenance is due as indicated by the condition of the oil. Among the parameters that are typically measured are oil temperature, contamination, and degradation. In a light vehicle, these sensors are usually mounted in the oil pan beneath the engine. The sensitivity of these sensors relies heavily on the surface area of the sensor. Thus, as the surface area increases, the signal strength increases.

The present invention recognizes that in order to increase the surface area, either the length of the sensor or the diameter of the sensor is increased. Because of sensor size considerations, it is often the length of the oil condition sensor that is increased instead of the diameter of the sensor. Unfortunately, in an oil pan, the length of the sensor is constrained by the depth of the pan. As such, the present invention understands that in deep oil pans the length of the sensor can be increased without problem, but in shallow oil pans increasing the length of the sensor can be problematic.

The present invention has recognized these prior art drawbacks, and has provided the below-disclosed solutions to one or more of the prior art deficiencies.

SUMMARY OF THE INVENTION

An oil sensor includes a first level sensing tube, and a common tube that surrounds the level sensing tube. A second level sensing tube surrounds the common tube. The second level sensing tube is electrically connected to the first level sensing tube and the common tube is separated from the first and second level sensing tubes.

In a preferred embodiment, the oil sensor includes a coupling/plug that is installed in the end of the first level sensing tube. A condition sensing tube is disposed around the coupling/plug. Accordingly, the coupling/plug insulates the condition sensing tube from the first level sensing tube. Preferably, tubes are concentric.

In a preferred embodiment, the sensor includes plural spacers that are installed between the first level sensing tube and the common tube and between the common tube and the second level sensing tube. Preferably, the sensor is disposed in a relatively shallow oil pan. Moreover, in a preferred embodiment, the sensor is connected to a control module. The control module receives signals from the sensor that represent the level and condition of oil in the oil pan. The control module is also connected to a warning device. The warning device receives a signal from the control module when the level of the oil or the condition of the oil falls outside a predetermined operating range.

In another aspect of the present invention, a vehicle oil lubricating system includes an engine and an oil pan. An oil sensor is disposed in the oil pan. In this aspect of the present invention, the oil sensor includes two level sensing tubes for sensing a level of oil in the oil pan and a condition sensing tube for sensing a condition of oil in the oil pan.

The present invention will now be described, by way of example, with reference to the accompanying drawings, in which:

BRIEF DESCRIPTION OF THE DRAWINGS

FIG. 1 is a block diagram representing an engine lubrication system;

FIG. 2 is an overhead view of an engine oil level/condition sensor; and

FIG. 3 is a cross-section view of an engine oil level/condition sensor taken along line 3—3 in FIG. 2.

DESCRIPTION OF AN EMBODIMENT OF THE INVENTION

Referring initially to FIG. 1, a vehicle lubrication system is shown and generally designated 10. FIG. 1 shows that the lubrication system includes an engine 12 and an oil pan 14 placed beneath the engine, in direct fluid communication with components located in the base of the engine 12, e.g., the pistons and crankshaft. The oil pan 14 also communicates with components in the top of the engine 12, e.g., the cylinder heads, via fluid line 16. As shown in FIG. 1, an oil pump 18 is installed along fluid line 16 so that it is in fluid communication with the engine 12 and the oil pan 14. Accordingly, the oil pump 18 pumps oil from the oil pan 14 to the, e.g., cylinder heads, in order to lubricate moving parts therein.

FIG. 1 also shows an oil condition sensor 20 disposed vertically in the oil pan 14 so that it is at least partially submerged in engine oil 22. As shown in FIG. 1, the oil condition sensor 20 is electrically connected to a control module 24 via electrically line 26. In turn, the control module 24 is connected to a warning device 28 via electrical line 30. The control module 24 uses the oil condition sensor 20 to monitor the level of oil 22 within the oil pan 14 and when the oil level falls below a predetermined minimum threshold, the control module 24 sends a signal to the warning device 28 to alert the driver that oil 22 needs to be added to the system 10. Additionally, the control module 24 uses the oil condition sensor 20 to monitor the condition of the oil 22 within the oil pan 14 and alert the driver, by sending an appropriate signal to the warning device 28, when the condition of the oil 22 falls outside a critical operating range. It is to be appreciated that the warning device 28 can be an audible warning device, e.g., a buzzer or audible alarm. On the other hand, the warning device 24 can be a visual warning device, e.g., a warning lamp or other visual display.

Referring now to FIGS. 2 and 3, details concerning the oil condition sensor 20 can be seen. FIGS. 2 and 3 show that the oil condition sensor 20 includes a generally cylindrical, first level sensing tube 32 surrounded by a slightly larger, generally cylindrical common tube 34. These tubes 32, 34 are then surrounded by a larger, generally cylindrical second level sensing tube 36. In a preferred embodiment, each of these tubes 32, 34, 36 are made from a conductive material, e.g., stainless steel. It is to be appreciated that the tubes 32, 34, 36 are concentrically placed around a central axis 38.

As shown in FIGS. 2 and 3, the first level sensing tube 32 is separated from the common tube 34 by a plurality of preferably non-conductive, relatively narrow spacers 40. In turn, the common tube 34 is separated from the second level sensing tube 36 by a plurality of preferably non-conductive, relatively large spacers 41. It is to be understood that the spacers 40, 41 maintain the concentricity of the tubes and electrically isolate the level sensing tubes 32, 36 from the common tube 34. The level sensing tubes 32, 36 are electrically connected to each other by a first wire 42 soldered or otherwise attached thereto.

Now referring to FIG. 3 only, it is shown that a solid, preferably plastic coupling/plug 44 is preferably press fitted into the lower end of the first level sensing tube 32. A first condition sensing tube 46 is press fitted around the coupling/plug 44 to form one integral tube having two portions: the first level sensing tube 32 and the first condition sensing tube 46. The coupling/plug 44 electrically isolates the first level sensing tube 32 from the condition sensing tube 46 and prevents fluid communication therebetween. FIG. 3 also shows a level sensing terminal lead 48 connected to the first level sensing tube 32, a condition sensing terminal lead 50 connected to the first condition sensing tube 46, and a common terminal lead 52 connected to the common tube 34. As stated above, the level sensing tubes 32, 36 are electrically connected by the first wire 42.

As shown in FIG. 3, a second condition sensing tube 54 is attached to the base of the second level sensing tube 36 by four of the relatively large spacers 41 which span the joint between the second condition sensing tube 54 and the second level sensing tube 36. The second level sensing tube 36 is electrically isolated from the second condition sensing tube 54 by a preferably non-conductive, ring-shaped insulator 56. It is to be appreciated that the ring-shaped insulator 56 can be integrally formed with the relatively larger spacers 41 that span the joint between the second level sensing tube 36 and the second condition sensing tube 54. FIG. 3 shows that the condition sensing tubes 46, 54 are electrically connected to each other by a second wire 58 soldered or otherwise attached thereto.

Accordingly, a signal can be applied to the level sensing tubes 32, 36 by the control module 24 via the level sensing terminal lead 48. The signal then passes through the oil 22 and returns via the common terminal lead 52. Electrical properties of the oil 22 affect the signal and any changes to the signal are used to determine the level of the oil. Similarly, a signal can be applied to the condition sensing tubes 46, 54 by the control module 24 via the condition sensing terminal lead 50 to determine the condition of the oil 22.

With the configuration of structure described above, it is to be appreciated that the oil condition sensor 20 described above provides increased sensing surface area by adding additional tubes to the sensor package instead of increasing the length of the sensor. Thus, the oil condition sensor 20 can be used in a shallow oil pan 14 to monitor the condition of oil 22 therein.

While the particular OIL CONDITION SENSOR as herein shown and described in detail is fully capable of attaining the above-described objects of the invention, it is to be understood that it is the presently preferred embodiment of the present invention and thus, is representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it is to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. section 112, sixth paragraph, unless the element is expressly recited using the phrase "means for."

We claim:

1. An oil sensor comprising:
   at least a first level sensing tube;
   at least a common tube surrounding the level sensing tube; and
   at least a second level sensing tube surrounding the common tube, the second level sensing tube being electrically connected to the first level sensing tube, the common tube being separated from the first and second level sensing tubes.

2. The oil sensor of claim 1, further comprising:
   a coupling/plug disposed in the end of the first level sensing tube; and
   at least a first condition sensing tube disposed around the coupling/plug, the coupling/plug electrically insulating the first condition sensing tube from the first level sensing tube.

3. The oil sensor of claim 2, further comprising:
   at least a second condition sensing tube attached to the second level sensing tube around the first condition sensing tube and the common tube, the second condition sensing tube being electrically insulated from the second level sensing tube and electrically connected to the first condition sensing tube.

4. The oil sensor of claim 1, wherein the tubes are concentric.

5. The oil sensor of claim 1, further comprising:
   plural spacers disposed between the first level sensing tube and the common tube; and
   plural spacers disposed between the common tube and the second level sensing tube.

6. The oil sensor of claim 1, wherein the sensor is disposed in a relatively shallow oil pan.

7. The oil sensor of claim 6, wherein the sensor is connected to a control module, the control module receiving a signal from the sensor representing a level of oil in the oil pan.

8. The oil sensor of claim 6, wherein the sensor is connected to a control module, the control module receiving a signal from the sensor representing a condition of oil in the oil pan.

9. The oil sensor of claim 7, wherein the control module is connected to a warning device, the warning device receiving a signal from the control module when the level of oil falls below a predetermined minimum.

10. The oil sensor of claim 8, wherein the control module is connected to a warning device, the warning device receiving a signal from the control module when the condition of the oil falls outside a predetermined operating range.

* * * * *